(12) United States Patent
Carpentier et al.

(10) Patent No.: US 12,029,652 B2
(45) Date of Patent: Jul. 9, 2024

(54) ASSEMBLY FOR IMAGING AND/OR TREATING BRAIN TISSUE

(71) Applicants: ASSISTANCE PUBLIQUE HOPITAUX DE PARIS, Paris (FR); SORBONNE UNIVERSITE, Paris (FR); CARTHERA, Paris (FR)

(72) Inventors: Alexandre Carpentier, Paris (FR); Guillaume Bouchoux, Lyons (FR); Michael Canney, Denver, CO (US); Francois Lacoste, Paris (FR)

(73) Assignees: ASSISTANCE PUBLIQUE HOPITAUX DE PARIS, Paris (FR); SORBONNE UNIVERSITY, Paris (FR); CARTHERA, Paris (FR)

( * ) Notice: Subject to any disclaimer, the term of this patent is extended or adjusted under 35 U.S.C. 154(b) by 324 days.

(21) Appl. No.: 16/623,974

(22) PCT Filed: Jun. 19, 2018

(86) PCT No.: PCT/EP2018/066203
§ 371 (c)(1),
(2) Date: Dec. 18, 2019

(87) PCT Pub. No.: WO2018/234280
PCT Pub. Date: Dec. 27, 2018

(65) Prior Publication Data
US 2020/0138580 A1    May 7, 2020

(30) Foreign Application Priority Data
Jun. 19, 2017   (FR) ...................................... 1755562

(51) Int. Cl.
*A61F 2/28*       (2006.01)
*A61B 8/00*       (2006.01)
(Continued)

(52) U.S. Cl.
CPC .......... *A61F 2/2875* (2013.01); *A61B 8/0808* (2013.01); *A61B 8/4281* (2013.01);
(Continued)

(58) Field of Classification Search
CPC ............. A61N 7/00; A61N 2007/0021; A61B 8/0808; A61B 2017/00924; A61B 8/4281;
(Continued)

(56) References Cited

U.S. PATENT DOCUMENTS

| 4,348,289 A | 9/1982 | Snavely et al. |
| 4,530,358 A | 7/1985 | Forssmann et al. |

(Continued)

FOREIGN PATENT DOCUMENTS

| EP | 2539021 B1 | 2/2016 |
| EP | 3020450 A1 | 5/2016 |

(Continued)

OTHER PUBLICATIONS https://www.rshydro.co.uk/sound-speeds/ RS Hydro, "Sound Speeds in Water, Liquid, and Materials", Sep. 2015 (Year: 2015).*

(Continued)

*Primary Examiner* — Sean D Mattson
*Assistant Examiner* — Michael Yiming Fang
(74) *Attorney, Agent, or Firm* — BCF LLP

(57) ABSTRACT

An assembly for imaging and/or treating brain tissue, having at least one acoustic window which comprises a plate that is transparent to ultrasonic waves, and at least one positioning marker which facilitates positioning of a probe for generating ultrasonic waves so as to be aligned with said acoustic window.

14 Claims, 5 Drawing Sheets

(51) Int. Cl.
*A61B 8/08* (2006.01)
*A61B 90/00* (2016.01)
*A61F 2/30* (2006.01)
*A61N 7/00* (2006.01)

(52) U.S. Cl.
CPC .............. *A61B 8/481* (2013.01); *A61B 90/39* (2016.02); *A61N 7/00* (2013.01); *A61B 2090/3925* (2016.02); *A61B 2090/3962* (2016.02); *A61F 2002/3009* (2013.01); *A61N 2007/0021* (2013.01); *A61N 2007/0052* (2013.01)

(58) Field of Classification Search
CPC ............ A61B 90/39; A61B 2090/3925; A61B 2090/3962; A61B 8/4209; A61B 8/4245; A61B 2017/00907; A61B 5/0059; A61B 5/0097; A61B 2090/3937; A61B 2090/3941; A61B 2090/3945; A61B 2090/3966; A61B 2090/3979; A61B 2090/3995; A61F 2/2875
See application file for complete search history.

(56) References Cited

U.S. PATENT DOCUMENTS

| | | | |
|---|---|---|---|
| 5,246,595 | A | 9/1993 | Bourlion et al. |
| 5,394,875 | A * | 3/1995 | Lewis .................. A61B 8/00 128/660 |
| 5,549,620 | A * | 8/1996 | Bremer .............. A61B 17/0643 411/338 |
| 6,350,284 | B1 * | 2/2002 | Tormala ................ A61F 2/2846 623/16.11 |
| 9,044,195 | B2 | 6/2015 | Manwaring et al. |
| 9,440,064 | B2 * | 9/2016 | Wingeier ............. A61B 5/4076 |
| 10,952,701 | B2 * | 3/2021 | Deffieux ............. A61B 8/4209 |
| 2005/0165312 | A1 | 7/2005 | Knowles et al. |
| 2007/0173844 | A1 * | 7/2007 | Ralph .................... A61B 17/68 |
| 2007/0260140 | A1 * | 11/2007 | Solar .................... A61B 90/39 600/426 |
| 2009/0227830 | A1 | 9/2009 | Pillutla et al. |
| 2010/0143241 | A1 | 6/2010 | Johnson et al. |
| 2010/0217160 | A1 | 8/2010 | Saguchi et al. |
| 2011/0312891 | A1 * | 12/2011 | Gestrelius .............. A61P 19/08 514/16.7 |
| 2012/0209150 | A1 | 8/2012 | Zeng et al. |
| 2013/0289411 | A1 | 10/2013 | Barnard et al. |
| 2014/0330123 | A1 * | 11/2014 | Manwaring ........ A61B 17/0643 411/338 |
| 2015/0321026 | A1 * | 11/2015 | Branson .................. A61N 7/02 |
| 2015/0360058 | A1 * | 12/2015 | Barthe .................... A61N 7/00 606/27 |
| 2017/0086785 | A1 * | 3/2017 | Bjaerum .............. A61B 8/4444 |
| 2017/0209274 | A1 * | 7/2017 | Beerens ................ A61F 2/2875 411/338 |
| 2019/0184204 | A1 * | 6/2019 | Ramamurthy ........... A61B 9/00 |

FOREIGN PATENT DOCUMENTS

| | | | |
|---|---|---|---|
| JP | 2010104656 | A * | 5/2010 |
| JP | 2017074293 | A * | 4/2017 ........... A61B 17/688 |
| WO | 89/07907 | A1 | 9/1989 |
| WO | 93/14712 | A1 | 8/1993 |
| WO | WO-2007056734 | A1 * | 5/2007 ............... A61N 7/00 |
| WO | 2007/064453 | A2 | 6/2007 |
| WO | 2014179720 | A1 | 11/2014 |
| WO | WO-2016012376 | A1 * | 1/2016 ........ A61F 2/30942 |
| WO | 2016202955 | A1 | 12/2016 |

OTHER PUBLICATIONS

Lucas VS, Burk RS, Creehan S, Grap MJ. Utility of high-frequency ultrasound: moving beyond the surface to detect changes in skin integrity. Plast Surg Nurs. Jan.-Mar. 2014; 34(1):34-8. doi: 10.1097/PSN.0000000000000031. PMID: 24583666; PMCID: PMC4027962. (Year: 2014).*

Ingraham CR, Mannelli L, Robinson JD, Linnau KF. Radiology of foreign bodies: how do we image them? Emerg Radiol. Aug. 2015; 22(4):425-30. doi: 10.1007/s10140-015-1294-9. Epub Feb. 4, 2015. PMID: 25648360 (Year: 2015).*

Amstutz C, Caversaccio M, Kowal J, Bächler R, Nolte LP, Häusler R, Styner M. A-mode ultrasound-based registration in computer-aided surgery of the skull. Arch Otolaryngol Head Neck Surg. Dec. 2003 (Year: 2003).*

Bing et al., "Blood-Brain Barrier (BBB) Disruption Using a Diagnostic Ultrasound Scanner and Definity® in Mice", Ultrasound Med. Biol., vol. 35, No. 8, pp. 1298-1308, 2009.

Carpentier et al., "Clinical trial of blood-brain barrier disruption by pulsed ultrasound", ScienceTranslationalMedicine, vol. 8, No. 343, 2016.

Eames et al., "Trans-cranial focused ultrasound without hair shaving: feasibility study in an ex vivo cadaver model", Journal of Therapeutic ultrasound, vol. 1, No. 24, 2013.

Guess et al., "Acoustic properties of some biocompatible polymers at body temperature", Ultrasound Med. & Biol., vol. 21, No. 2, pp. 273-277, 1995.

Hynynen et al., "Noninvasive MR Imaging-guided Focal Opening of the Blood-Brain Barrier in Rabbits", Radiology, vol. 220, N. 3, pp. 640-646, 2001.

Marquet et al., "Noninvasive, Transient and Selective Blood-Brain Barrier Opening in Non-Human Primates In Vivo" PLOS One, vol. 6, No. 7, 2011.

McDannold et al., "Temporary Disruption of the Blood-Brain Barrier by Use of Ultrasound and Microbubbles: Safety and Efficacy Evaluation in Rhesus Macaques", Cancer Res., vol. 72, No. 14, pp. 3652-3663, 2012.

Melamed et al., "Sonographic Appearance of Oxidized Cellulose (Surgicel): Pitfall in the Diagnosis of Postoperative Abscess", J. Ultrasound Med., vol. 14, No. 1, pp. 27-30, Jan. 1995.

Raymond et al., "Acoustic Transmission Losses and Field Alterations Due to Human Scalp Hair", IEEE Transactions on Ultrasonics, Ferroelectrics, and Frequency Control, vol. 52, No. 8, pp. 1415-1419, Aug. 2005.

Sparing et al., "Transcranial Magnetic Stimulation and the Challenge of Coil Placement: A Comparison of Conventional and Stereotaxic Neuronavigational Strategies", Human Brain Mapping, vol. 29, No. 1, pp. 82-96, Jan. 2008.

Tobias et al., "An ultrasound window to perform scanned, focused ultrasound hyperthermia treatments of brain tumors", Medical Physics, vol. 14, No. 2. pp. 228-234, 1987.

Van der Bom et al., "Frameless multimodal image guidance of localized convection-enhanced delivery of therapeutics In the brain", J. Neurointerv. Surg., vol. 5, No. 1, pp. 69-72, Jan. 2013.

Wei et al., "Neuronavigation-Guided Focused Ultrasound-Induced Clood-Brain Barrier Opening: A Preliminary Study in Swine", AJNR. Am. J. Neuroradiol., vol. 34, No. 1, pp. 115-120, Jan. 2013.

* cited by examiner

ASSEMBLY FOR IMAGING AND/OR TREATING BRAIN TISSUE

CROSS-REFERENCE TO RELATED APPLICATIONS

This application is a national phase filing under 35 U.S.C. § 371 of International Application No. PCT/EP2018/066203 filed on Jun. 19, 2018, which claims benefit of priority from French Patent Application No. 1755562 filed Jun. 19, 2017, the contents of which are hereby incorporated by reference in their entirety.

FIELD OF THE INVENTION

The present invention relates to the general technical field of the ultrasonic devices for imaging and/or treating a human or animal brain tissue by ultrasounds in order to assist a practitioner in establishing a diagnosis and/or in order to treat a pathology.

BACKGROUND OF THE INVENTION

Various techniques for imaging or treating a brain tissue are known.
1. Imaging
Brain imaging (or neuro-imaging) can be used to allow the practitioner to follow the progression of a brain injury or a brain tumor for diagnosis and/or surgical procedure purposes.

The most commonly used imaging techniques are the computed tomography (commonly called scanner) and the magnetic resonance imaging (MRI). Although these techniques are effective, they have disadvantages. In particular, the computed tomography is becoming less and less used because of the risks of neoplasia. The magnetic resonance imaging has a high cost and requires the injection of a contrast agent to the patient.

It is therefore desirable to have an alternative technique to enable brain imaging.

Imaging techniques based on the use of ultrasounds for imaging a brain tissue are also known. However, these techniques face the difficulty of transmitting ultrasounds through the cranium of the patient.
2. Treatment
Various techniques for treating a brain tissue, in particular by ultrasounds, are known.

Document EP 2 539 021 for example describes an apparatus for treating disorders of the brain comprising:
  an implantable ultrasonic device made of non-ferromagnetic material,
  a control unit remote from the ultrasonic device, and,
  connection means between the ultrasonic device and the control unit.

The operating principle of this apparatus is as follows. Once the ultrasonic device is implanted into the skull of the patient, a succession of treatment sessions are provided to the latter to treat the pathology affecting him. At each new treatment session, the intracorporeal device is connected to the control unit via the connection means.

Even if the apparatus described in document EP 2 539 021 enables an effective treatment of brain disorders, it would be desirable to have an alternative treatment technique for applying ultrasounds from outside the skull so as to simplify the work of the practitioner, the installation of the connection means between the ultrasonic device and the control unit can sometimes be difficult to implement.

In addition, an outer ultrasonic device can have the following advantages:
  non-implantable device, therefore easier to manufacture, no problems of sterility or MRI compatibility,
  the ultrasonic emitter may be more complex than what is achievable in an implantable version; for example, an outer emitter may have multiple channels, allowing matching by electronics the shape of the beam to the target,
  possibility to reach multiple areas of the brain by orienting the ultrasonic emission relative to the tissue; possibility to focus the acoustic waves in a particular area of the brain; possibility to scan an area by displacing the acoustic beam; in some cases therefore the window may be smaller than the area to be treated;
  Once the window is implanted into the patient, it is possible to adapt the acoustic emitter, for example to best counter the progression of the disease (treatment of a local relapse area for example)

Other apparatuses for treating and/or imaging a brain tissue are also known.

Document WO2016202955 describes a detection apparatus for imaging at least two areas of a brain of a subject. The detection apparatus comprises a support including a frame intended to be attached to the skull of the subject, the frame delimiting an inner portion which is transparent to the ultrasonic waves. The detection apparatus also comprises a removable imaging device including a platform, an ultrasonic probe, a movable plate supporting the ultrasonic probe, and a fastener intended to cooperate with three pins of the support to temporarily lock the plateform to the support. However such an apparatus is not implantable under the skin of the subject's skull.

Document US2014/0330123 describes a sonic window adapted to close an opening formed in the skull of a patient. The sonic window comprises an outer surface and an inner surface each including holes. However, such a sonic window is difficult to locate once implanted and covered with the skin of the subject's skull.

Document US2015/0321026 describes a device for regulating the focal depth of an ultrasonic energy emitted for treating or imaging a tissue. The regulation device comprises an ultrasonic transducer and a spacer intended to be positioned between the ultrasonic transducer and the patient's skin. Elements may be provided in the spacer, these elements having an acoustic impedance different from that of the spacer to favor or block the passage of the ultrasonic waves. However, such a regulation device is not implantable.

An object of the present invention is to propose an assembly for imaging and/or treating a brain tissue by ultrasounds making it possible to overcome at least one of the aforementioned disadvantages.

SUMMARY

For this purpose, the invention proposes an assembly for imaging and/or treating a brain tissue comprising:
  at least one acoustic window intended to be implanted at an opening arranged into the cranium of a patient, said acoustic window being covered with the skin of the patient's skull once implanted, and,
  an ultrasonic wave generation probe intended to be positioned in line with the acoustic window,
remarkable in that the acoustic window comprises a plate transparent to the ultrasonic waves and at least one positioning mark locatable through the skin of the patient's skull to facilitate the positioning of the probe in line with said acoustic window prior to the generation of the ultrasonic waves.

Document WO2016202955 does not describe an assembly in which the acoustic window is intended to be covered with skin once implanted. Furthermore, document WO2016202955 does not describe an assembly in which the acoustic window comprises a positioning mark locatable through the skin of the patient's skull. Indeed, the three pins of the support do not constitute positioning marks. On the contrary, these pins form, with the element for attaching the platform, means for locking temporarily the platform 16 on the frame 14. Moreover, no positioning mark is necessary in the detection apparatus according to document WO2016202955 since the window is not intended to be implanted under the skin of the skull of the subject to be treated.

Document US2014/0330123 does not describe an assembly in which an acoustic window comprises a positioning mark locatable through the skin of the patient's skull. On the contrary, in document US2014/0330123, the holes constitute, with the anchoring elements, means for attaching the sonic window in the opening formed through the skull of the patient.

Document US2015/0321026 does not describe an assembly in which the acoustic window is intended to be covered with skin once implanted. Furthermore, Document US2015/0321026 does not describe an acoustic window including one (or more) positioning mark(s) locatable through the skin of the patient's skull. On the contrary, in document US2015/0321026, the spacer (including the elements of acoustic impedance different from that of the spacer) is intended to be positioned on the skin. Furthermore, document US2015/0321026 does not teach those skilled in the art that the integration of a positioning mark locatable through the skin of the skull—such as a marker visible by ultrasonography—to an implantable window can favor its detection once it is implanted (and covered with the skin of the patient's skull).

Preferred but non-limiting aspects of the present invention are as follows:
- the acoustic window may comprise a plurality of unit positioning marks different from each other,
- at least one positioning mark may be a mechanical part locatable through the skin of the patient by touch,
- the mechanical part may consist of a pin extending outwardly from an upper face of the plate,
- at least one positioning mark may be an marker visible by optics, in particular by infra-red, or by ultrasonography or by magnetic resonance imaging,
- the marker may comprise an echogenic structure,
- at least two positioning marks may consist of markers visible by optics or by ultrasonography or by magnetic resonance imaging, each marker including:
  - a substrate having a first acoustic impedance, and
  - an element having a second acoustic impedance, the elements extending to different depths in the substrate,
- at least two positioning marks may consist of markers visible by optics or by ultrasonography or by magnetic resonance imaging, each marker consisting of a blind hole of different depth,
- the thickness of the plate may be chosen equal to an integer multiple of half the wavelength in the plate of the ultrasonic waves generated by the probe,
- the plate may be composed of a superposition of layers of different materials, said superposition including at least one rigid material layer and at least one flexible material layer,
- the window may comprise mechanical reinforcements extending at the periphery of the plate.

BRIEF DESCRIPTION OF THE DRAWINGS

Other advantages and characteristics of the assembly for imaging and/or treating a brain tissue will become more apparent from the following description of several variants, given by way of non-limiting examples, from the appended drawings in which.

DETAILED DESCRIPTION OF THE INVENTION

Figure 1:
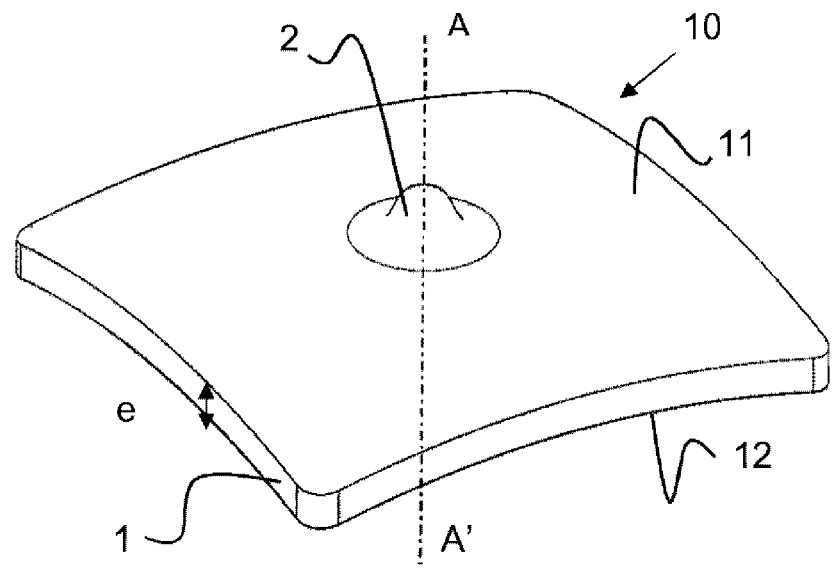
FIGS. 1, 3, 5 et 6 schematically illustrate different embodiments of an acoustic window, FIGS. 2, 4 schematically illustrate the acoustic windows once implanted into the skull of a patient, FIGS. 7 and 8 schematically illustrate a mode of detection of markers for centering an acoustic window.

Various examples of assemblies for imaging and/or treating a brain tissue with reference to FIGS. 1 to 9 will now be described. In these different figures, the equivalent elements are designated by the same reference number.

1. General Principle

The assembly for imaging and/or treating a brain tissue comprises:
- An acoustic window 10, and
- A probe able to generate ultrasonic waves.

This assembly allows a practitioner to check the progression of a brain tissue by imaging and/or to treat the brain tissue by using ultrasounds.

The probe is intended to be handled by the practitioner. It comprises a casing in which is housed at least one transducer (not represented) for the generation of ultrasonic waves.

The window 10 is intended to be implanted into the patient, in particular at an opening arranged in his cranium 4. This provides a protection to the brain and prevents its deformation due to pressure changes.

In the following, the window 10 and the probe will be described in more detail with reference to FIGS. 1 to 9.

2. Acoustic Window

FIGS. 1 to 6 illustrate different examples of acoustic windows 10 used to close an opening arranged in the cranium 4 of a patient for ultrasound imaging and/or treatment purposes.

The window 10 comprises a plate 1 and one (or more) positioning mark(s) 2 for detecting the center of the plate 1 once the window 10 is implanted.

2.1. Plate

The plate 1 may be substantially flat. Alternatively, the plate 1 may be curved to follow the curvature of the cranium 4 of the patient. In particular, the plate can be made by three-dimensional printing, its shape being provided to follow the curvature of the patient's skull.

The plate 1 is advantageously made of an acoustically transparent material to enables the passage of the ultrasonic waves through the window 10 in order to image and/or treat a brain tissue.

The material chosen to constitute the plate 1 has preferably a low acoustic absorption to limit the heating of the window 10 during the emission of ultrasonic waves by the probe. Indeed, during the passage of the ultrasonic waves through the window 10, a portion of the energy is absorbed by the plate 1. This absorbed energy is converted into heat. By choosing a material having a low acoustic absorption to constitute the plate 1, the risks of heating of the window 10 and therefore burning of the patient are limited.

The material chosen to constitute the plate 1 further has preferably an acoustic impedance close to 1.5 Mega-Rayleigh to limit the reflections of the acoustic wave on the window. By choosing a material having an acoustic impedance close to 1.5 Mega-Rayleigh to constitute the plate 1, it is made sure that all the acoustic energy emitted by the probe enters the window and, if the latter is not very absorbent, the brain tissue.

Preferably, the material chosen to constitute the plate 1 is rigid, non-brittle and has a high thermal conductivity (to favor the evacuation of heat generated during the passage of the ultrasonic waves through the window 10 and in the brain tissue).

For example, the material can be:
- a polymeric material such as polyethylene, polystyrene, acrylic, polyetheretherketone (PEEK) or poly(methyl methacrylate) (PMMA),
- a thermoplastic elastomer such as PEBAX.

The plate 1 is generally rectangular, but it should be noted that the plate 1 may have any shape, such as a circular shape. The dimensions of the plate 1 (length and width) can be comprised between 1 and 15 centimeters. In particular, the dimensions of the acoustic window may vary depending on the depth of the brain tissue (in particular a tumor) to be treated or imaged. For example, in the case of a deep tumor, the dimensions of the acoustic window may be smaller than the dimensions of the tumor, whereas in the case of a superficial tumor (i.e. close to the cranium), the dimensions of the window will be preferably equal to (or greater than) the dimensions of the tumor.

Indeed, in the case of a deep tumor, it is possible to treat the entire tumor from an acoustic window (of smaller dimensions than the tumor) by varying the orientation of the probe. Thus, in the case of a deep tumor, it is possible to treat the entire surface of the tumor by emitting ultrasonic waves at different angles of incidence. Advantageously, the acoustic window will be chosen as small as possible by taking into account the dimensions of the area to be treated, its depth and the possibility of inclining the emission of the ultrasounds with respect to the window.

Advantageously, the thickness "e" of the plate 1 is chosen equal to an integer multiple of half the wavelength in the plate 1, of the ultrasonic waves generated by the probe. This makes it possible to improve the coefficient of transmission of the ultrasonic waves in the plate 1, even in the event of significant impedance mismatch between the impedance of the material constituting the plate 1 and the external environment.

In some variants, the plate 1 is composed of a superposition of layers of different materials transparent to the ultrasonic waves. For example, in one variant, the plate 1 is composed of a rigid material layer extending between two flexible material layers:
- the rigid material layer makes it possible to increase the mechanical strength of the plate 1, while
- the flexible material layers make it possible to limit the risks of dispersion of pieces of the rigid material layer in the event of breakage of the latter.

The window may also comprise one (or more) acoustic impedance matching layer(s). The acoustic impedance matching layer(s) is/are made of a material—such as parylene or silicone—whose acoustic impedance is comprised between the impedance of the transducers of the probe and the acoustic impedance of the target area. The presence of matching layers makes it possible to limit the reflections of ultrasonic waves at the interface between the transducer 21 and the acoustic window and between the window and the tissue. If the window is made of a relatively "heavy" and thick material to be mechanically solid (for example epoxy, or even ceramic) and if the reflection coefficient is high, to limit the reflection, it is possible to add a layer (or two, one on each side) of a quarter of the wavelength of thickness, and ideally of impedance $(Zplate \times Zwater)^{0.5}$ according to the well-known formula. This material may for example be a silicone (if the plate is made of epoxy) or made of epoxy (if the plate is made of ceramic or metal). More generally, it is possible to optimize a multilayer structure to have a low reflection coefficient and good mechanical rigidity by choosing the appropriate thicknesses and materials. Another solution is to use an exactly thick window of the wavelength divided by 2 without a quarter-wave plate.

The window 10 may also comprise reinforcements for increasing the mechanical strength of the plate 1. The reinforcements extend for example at the edges of the plate 1.

The reinforcements may consist of rods made of rigid material—such as titanium or stainless steel or any other biocompatible metal known to those skilled in the art—integrated in the plate 1.

Alternatively, the reinforcements may be made of the same material as the plate 1. For example, the reinforcements may consist of one (or more) peripheral area(s) of the plate 1 having a thickness/thicknesses greater than the thickness of a central area of the plate 1. Thus, the plate can comprise thick areas for reinforcing its mechanical strength and thinned areas for a better transmission of the ultrasonic waves.

Different solutions can be adopted for the implantation of the plate 1 previously described into the skull of the patient. In particular, the plate 1 can be implanted:
- so as to extend in the extension of the cranium of the patient (see FIGS. 1-2 and FIGS. 5-6), or
- so as to extend above the cranium of the patient (see FIGS. 3-4).

2.1.1. First Variant of Implantation of the Acoustic Window

Figure 2:
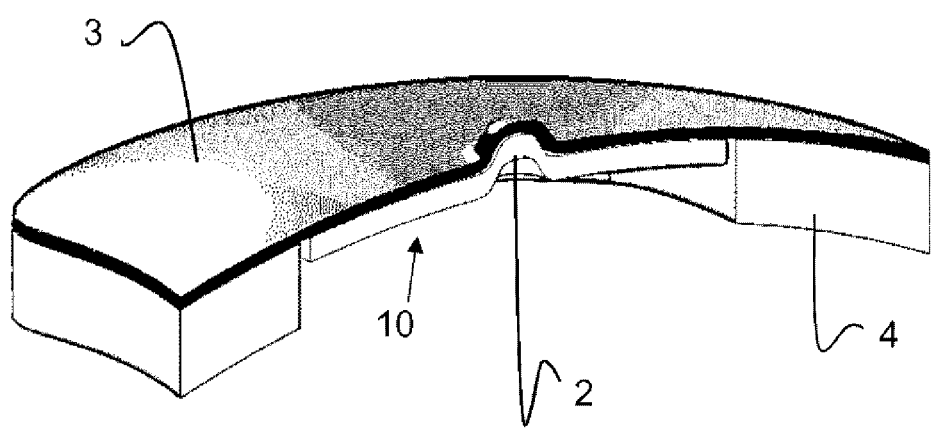

In the embodiment illustrated in FIGS. 1 and 2 (and in FIGS. 5 and 6), the plate 1 is adapted to be flush with the opening arranged in the cranium of the patient. The dimensions and shape of the plate 1 are adapted to the dimensions and shape of the opening that has been formed through the cranium 4 of the patient.

The window 10 illustrated in FIG. 1 can be attached to the cranium 4 by gluing, for example using an adhesive—such as cyanoacrylate. In this case, the adhesive is applied to the lateral edges of the plate 1, and the latter is press-fitted into the opening formed through the cranium 4. Once the adhesive is cured, the window 10 is secured to the cranium 4. Of course, the window can be attached to the cranium 4 by using any other means known to those skilled in the art such as attachment brackets (not represented).

As illustrated in FIG. 2, this solution allows making the window 10 almost "invisible" once the window 10 is covered with the skin 3, the latter extending in the extension of the cranium 4.

2.1.2. Second Variant of Implantation of the Acoustic Window

Figure 3:
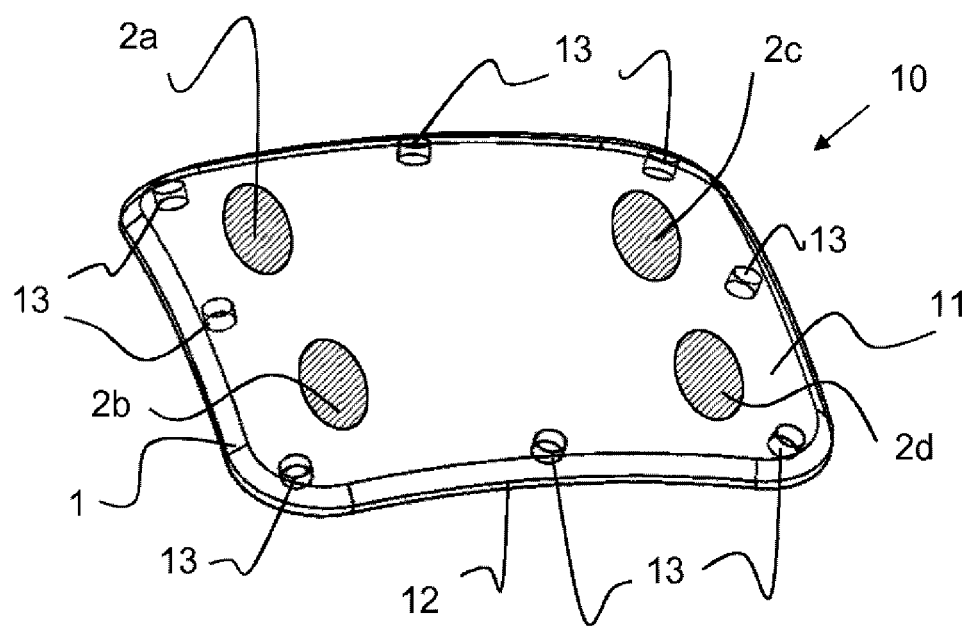
Figure 4:
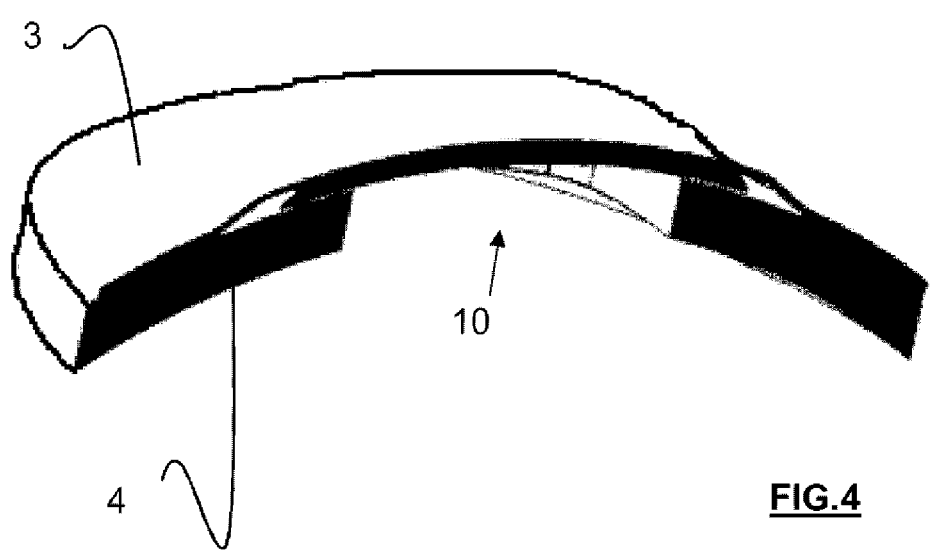

Alternatively, the acoustic window may be adapted to cover the opening while extending above the cranium of the patient (see FIGS. 3-4).

In this variant, the acoustic window comprises through holes 13 arranged between the upper 11 and lower 12 faces of the plate 1. These holes 13 extend at the periphery of the plate 1, along each edge of the plate. The holes 13 are intended to receive attachment elements—such as bone anchoring screws—for attaching the window 10 on the cranium 4.

In this variant of implantation and as illustrated in FIG. 4, the dimensions of the plate 1 are greater than the dimensions of the opening arranged in the cranium 4 so that the window 10 is intended to be attached to the cranium 4.

This embodiment allows reducing the constraints for the practitioner in making the opening arranged in the cranium. Indeed, the practitioner does no longer have to make an opening at dimensions and shape very accurate with respect to the dimensions and shape of the plate 1.

2.2. Positioning Mark(s)

The window 10 also comprises one (or more) positioning mark(s) 2. The positioning mark(s) allow(s) the practitioner to identify the position of the plate 1 and thus to position the probe in line with said plate 1 in order to image and/or treat an underlying brain tissue. The use of positioning marks makes it possible to reduce the time required to implement a session for imaging and/or treating the cerebral area, in particular with respect to a solution based on the use of a neuro-navigation assembly.

Indeed, without this positioning mark 2, it would be difficult for the practitioner to accurately identify the position of the window 10 once the latter is implanted, the window 10 being covered with the skin 3 of the patient's skull. However, the knowledge of the accurate position of the window 10 is necessary to ensure proper positioning of the probe above the plate 1.

As will be described in more detail below, each positioning mark may consist of:
- A mechanical element, locatable through the skin of the patient by touch from the operator, or
- A position marker visible by ultrasounds, or
- A position marker visible by MRI.
- A position marker visible by optics, for example in the infrared range.

The choice among these different types of positioning marks is independent of the variant of implantation chosen for the acoustic window (i.e. acoustic window extending in the extension of the cranium or above the cranium). Moreover, these different types of positioning mark can be used in combination in the same acoustic window 10.

Advantageously, when the window comprises several positioning marks disposed on a plate, these can all be different. This facilitates the repeatability of the positioning and orientation of the probe during successive sessions for imaging and/or treating a brain tissue.

2.2.1. First Example of a Positioning Mark

In the embodiment illustrated in FIGS. 1 and 2, the positioning mark 2 is a mechanical element. The positioning mark 2 consists of a pin extending outwardly at the upper face 11 of the plate 1. This allows revealing a protrusion on the skin 3 covering the pin.

Referring to FIG. 1, the window comprises a single pin disposed in the center of the plate 1.

Alternatively, the window 10 may comprise several pins (in particular two, three, four, etc.). For example, the window 10 may comprise four pins 2 disposed in the vicinity of the corners of the rectangular plate 1 on the upper surface 11 of the plate.

Of course, the shape and dimensions of the mechanical positioning mark may vary depending on the application. For example, the positioning mark may consist of a crater whose peripheral edges extend outwardly of the plate and whose central region is hollowed out within the thickness of the plate.

2.2.2. Second Example of a Positioning Mark

FIGS. 3, 4, 5, and 6 illustrate a second example of a positioning mark.

In this embodiment, the window 10 comprises centering markers 2a, 2b, 2c, 2d (respectively 21 to 24 and 25 to 27) visible by ultrasounds, optics or MRI.

Figure 5:
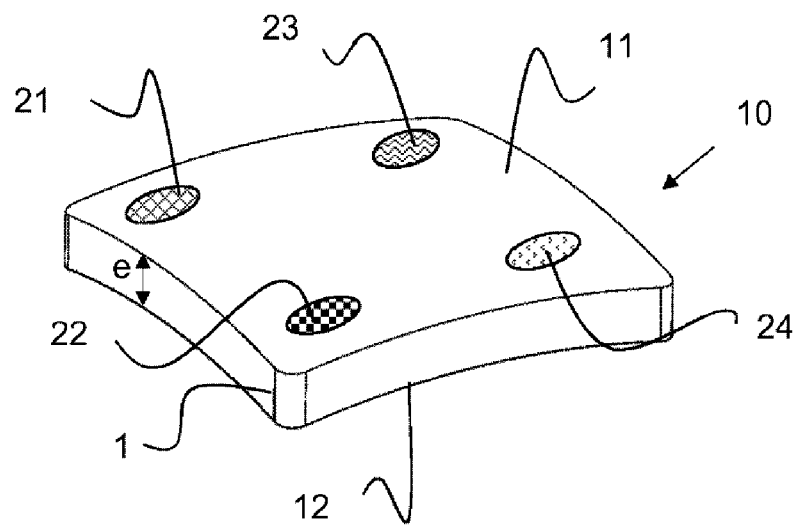

In the variants illustrated in FIGS. 3 and 5, the window 10 comprises four centering markers 2a, 2b, 2c, 2d (respectively 21 to 24) disposed at the four corners of the rectangular plate 1. Each centering marker consists for example of a metal structure or a hard echogenic plastic structure.

Figure 6:
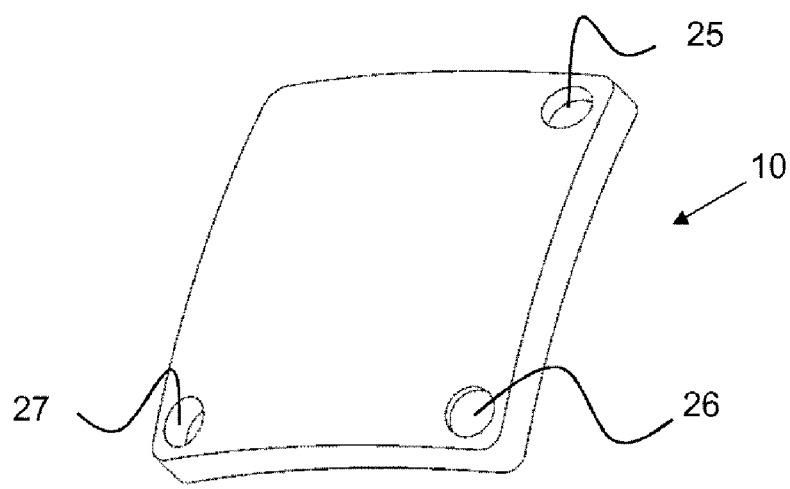

In the variant illustrated in FIG. 6, the window comprises three centering markers 25, 26, 27 disposed at three corners of the rectangular plate 1. Each centering marker consists for example of a blind or through hole.

The use of centering markers makes it possible to have markers integrated into the plate 1 without protrusion on the upper face 11 of the plate 1.

These centering markers are for example detectable by using the transducers of the imaging and/or treatment probe in A-mode ultrasonography (also called "A-scan" or "A-mode"). The A-mode ultrasonography is based on the emission of an acoustic information and the reception of echoes along a propagation line. Alternatively, the probe may comprise specific transceivers (operating in A-mode) enabling the detection of the centering markers.

Once the position of the centering markers is detected using the probe, the latter can be positioned accurately above the window 10 prior to the application of ultrasonic waves to image or treat a brain tissue.

The markers detectable by ultrasounds or by optics can coexist with markers detectable by MRI. Advantageously, the first ones are in a known geometric relationship with the second ones.

In the embodiment illustrated in FIGS. 3 and 4, the centering markers are all identical.

Alternatively, the centering markers detectable by ultrasounds, optics or MRI may all be different, as illustrated in FIGS. 5 and 6. This allows the practitioner to identify each centering marker individually.

More precisely in the embodiment illustrated in FIG. 5, each marker 21, 22, 23, 24 comprises a substrate 210, 220, 230, 240 having a first acoustic impedance and an element 213, 223, 233, 243 having a second acoustic impedance. For each marker 21, 22, 23, 24, the second acoustic impedance element 213, 223, 233, 243 is buried at a different depth in the substrate 210, 220, 230, 240 so that the distribution of the elements 213, 223, 233, 243 in the substrate 210, 220, 230, 240 constitutes a code enabling the identification of said marker 21, 22, 23, 24.

In the embodiment illustrated in FIG. 6, each centering marker consists of a blind hole of identical diameter and different depth; more precisely, the window comprises:
- a first blind hole with a depth of 1 millimeter,
- a second blind hole with a depth of 2 millimeters, and
- a third blind hole with a depth of 3 millimeters.

Figure 8:
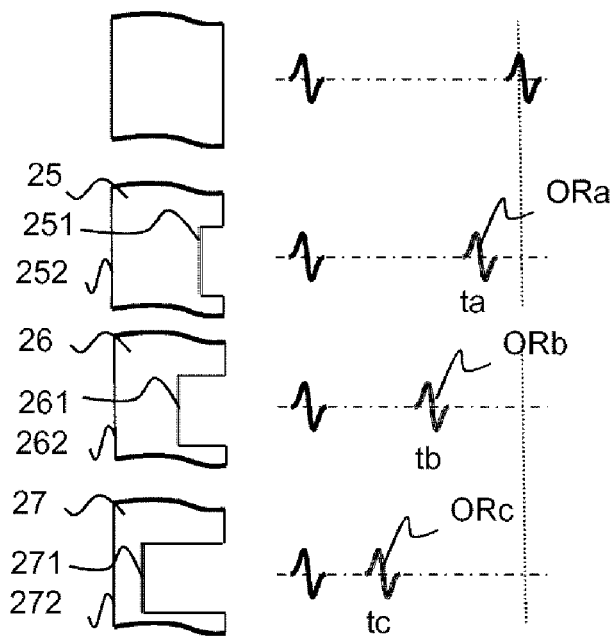

Even if one-millimeter variations between the different blind holes are difficult to identify by touch, they can be detected by using the transducers of the probe in A-mode ultrasonography, these recording the waves reflected by the blind holes at different times (see FIG. 8). The blind holes can also be localized using an imaging ultrasonographic probe.

The embodiments illustrated in FIGS. 5 and 6 make it possible to define a depth coding making it possible to distinguish the markers from each other.

2.2.3. Modes of Detection of the Centering Markers Illustrated in FIGS. 5 and 6

Figure 7:
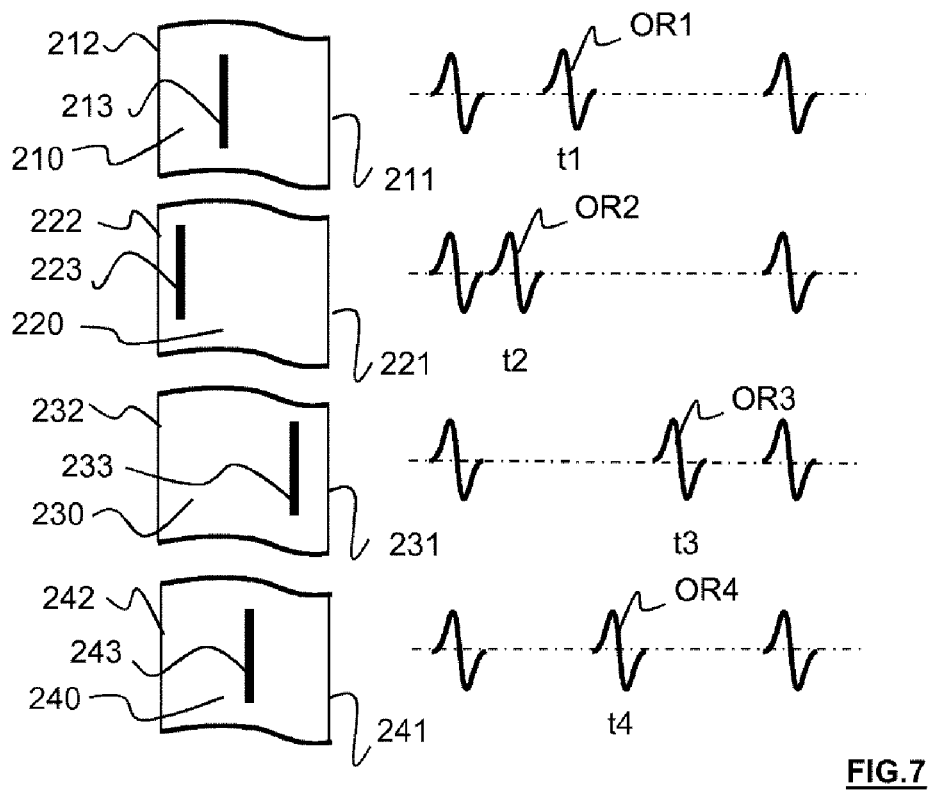

FIG. 7 illustrates a mode of detection of the four markers 21, 22, 23, 24 represented in FIG. 5 and each including an element 213, 223, 233, 243 disposed in a substrate 210, 220, 230, 240, the second acoustic impedance elements extending at different depths in the substrate:

the front face 211, 221, 231, 241 of the substrate 210, 220, 230, 240 constitutes a first ultrasound reflector (because of the difference in acoustic impedance between the substrate and the tissue in contact with the front face), this front face extending on the upper face 11 of the plate 1, the rear face 212, 222, 232, 242 of the substrate 210, 220, 230, 240 constitutes a second ultrasound reflector (because of the difference in acoustic impedance between the substrate and the tissue in contact with the rear face), this rear face extending on the lower face 12 of the plate 1, and the second acoustic impedance element 213, 223, 233, 243—which may consist of a gaseous inclusion in the body of the substrate—constitutes a third ultrasound reflector extending between the front 211, 221, 231, 241 and rear 212, 222, 232, 242 faces.

When using the probe in A-mode ultrasonography, the reflected waves OR1, OR2, OR3, OR4 by the elements 213, 223, 233, 243 are recorded by the probe at different times t1, t2, t3, t4 relative to the times of recording the waves reflected by the first and second reflectors 211, 221, 231, 241 and 212, 222, 232, 242.

Thus, it is possible to distinguish the different markers 21, 22, 23, 24 when the practitioner searches the position of the window 10. This facilitates the introduction of the probe in line with the window 10.

FIG. 8 illustrates a mode of detection of the three markers 25, 26, 27 represented in FIG. 6 and each consisting of a blind hole of different depth:

the bottom 251, 261, 271 of each blind hole constitutes a first ultrasound reflector, the rear face 252, 262, 272 of the plate constitutes a second ultrasound reflector.

When using the probe in A-mode ultrasonography, the reflected waves ORa, ORb, ORc by the bottoms 251, 261, 271 of the blind holes are recorded by the probe at different times ta, tb, tc relative to the times of recording the waves reflected by the rear face of the plate.

Thus, it is possible to distinguish the different markers 25, 26, 27 when the practitioner searches the position of the window 10 in order to facilitate the introduction of the probe to perform the treatment.

3. Operating Principle

Figure 9:
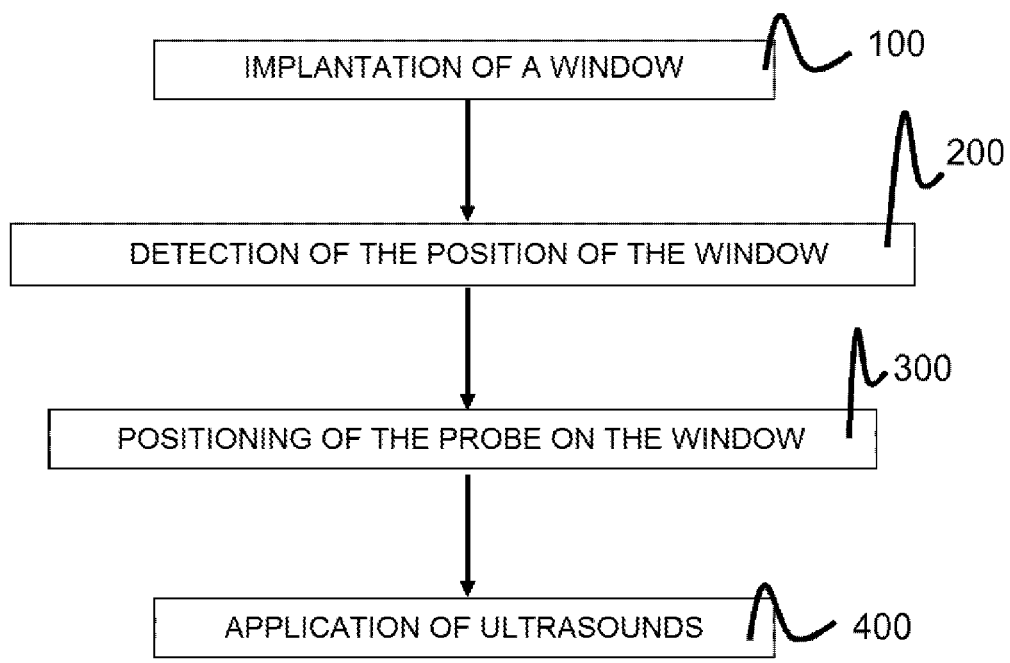
FIG. 9 illustrates an example of a method for treating a pathology by means of an assembly for treating a brain tissue.

The operating principle of the assembly for imaging and/or treating a brain tissue will be now described with reference to FIG. 9. It will be considered in the following that the assembly comprises a window 10 according to the third embodiment.

In a first step, the practitioner implants (step 100) the window 10 into the skull of the patient. He makes one (or more) opening(s) in the skull of the patient, and attaches a window 10 in the opening (or in each respective opening) by gluing or anchoring. When implanting the window, the practitioner can fill the free space between the window 10 and the dura mater with a suitable material (gel or saline solution). The practitioner then covers the window with the skin 3 of the patient. Advantageously, the incision of the patient's skin is practiced so as to prevent the scar resulting from the closuring of the skin after implantation of the window from covering the window (the quality of ultrasonic wave transmission being reduced through the scars).

Once the window is implanted, a succession of sessions for imaging and/or treating a brain tissue can be provided to the patient.

At each new treatment session, the practitioner implements a step of detecting (step 200) the position of the window 10. It switches the probe into a location mode (transducers of the probe or specific transceivers activated in A-mode ultrasonography), applies a transmission gel for ultrasonography on the patient's hair, and displaces the probe over the patient's skull to detect the position of the window 10.

When the probe detects one of the centering markers 21, 22, 23, 24, a processing unit connected to the probe sends information to inform to the practitioner that a centering marker has been detected.

Since the markers are all different, the processing unit can define which of the centering markers has been detected and provide information to the practitioner on the direction in which it is preferable to displace the probe to detect the other three centering markers. For example, if the detected centering marker is the marker disposed in the upper left corner of the window 10, the processing unit instructs the practitioner to displace the probe in a downward and rightward direction.

When the four centering markers are detected, the processing unit sends information to the practitioner asking him to hold the probe stationary. Optionally, the probe may be removed to reapply transmission gel on the patient's hair above the window before repositioning (step 300) the probe in line with the window 10.

Once the probe is positioned, the practitioner switches the mode of operation of the probe from the location mode to a treatment or imaging mode. The transducers are activated to allow imaging or treating the brain tissue (step 400).

The reader will have understood that many modifications can be made to the invention described above without physically departing from the new teachings and advantages described herein.

For example, in the foregoing description, the positioning marks were:

either a mechanical element, locatable through the skin of the patient by touch from the operator, or or a position marker visible by ultrasounds, or a position marker visible by MRI.

or a position marker visible by optics, for example in the infrared range.

Of course, each positioning mark could consist of an element locatable by touch and detectable and by ultrasounds and/or MRI. Moreover, one (or more) positioning mark(s) detectable by ultrasounds or MRI may be combined with one or more mechanical element(s) locatable by touch or by optics within the same acoustic window.

Accordingly, any modifications of this type are intended to be incorporated within the scope of the attached claims.

The invention claimed is:

1. An assembly for imaging and/or treating a brain tissue comprising:
   at least one acoustic window configured to be implanted at an opening arranged into the cranium of a patient, and configured to be covered with the skin of the patient's skull once implanted;
   an ultrasonic wave generation probe intended to be positioned in line with the acoustic window,
   wherein the acoustic window comprises:
      a plate transparent to ultrasonic waves, and
      a plurality of positioning marks configured to be locatable through the skin of the patient in order to facilitate the positioning of the probe in line with said acoustic window,
      each of the plurality of positioning marks being configured to return a reflection time detectable by the ultrasonic wave generation probe; and
   a processing unit communicatively connected to the ultrasonic wave generation probe, the processing unit being configured to:
      determine which of the plurality of positioning marks has been detected based on the reflection time, and
      display an instruction to displace the ultrasonic wave generation probe in a specified direction based on which of the plurality of positioning marks has been detected.

2. The assembly according to claim 1, wherein the plate is composed of a superposition of layers of different materials, said superposition including at least one rigid material layer and at least one flexible material layer.

3. The assembly according to claim 1, wherein the acoustic window comprises mechanical reinforcements extending at a periphery of the plate.

4. The assembly according to claim 1, wherein at least one of the plurality of positioning marks is a marker visible by ultrasonography.

5. The assembly according to claim 4, wherein the marker comprises a plastic echogenic structure visible by ultrasonography.

6. The assembly of claim 1, wherein each of the plurality of positioning marks comprises a blind hole having a different depth from any other positioning mark of the plurality of positioning marks.

7. The assembly of claim 1, wherein at least one of the plurality of positioning marks is located at the center of the plate and integrated on or within the plate.

8. An assembly for imaging or treating a brain tissue, the assembly comprising:
   at least one acoustic window configured to be implanted at an opening arranged into the cranium of a patient, and configured to be covered with the skin of the patient's skull once implanted;
   an ultrasonic wave generation probe intended to be positioned in line with the acoustic window,
   wherein the acoustic window comprises a plate transparent to ultrasonic waves, and wherein the plate comprises:
      a first plurality of positioning marks detectable by ultrasonography, and
      a second plurality of positioning marks detectable by magnetic resonance imaging (MRI),
      each of the first plurality of positioning marks being configured to return a reflection time detectable by the ultrasonic wave generation probe; and
   a processing unit communicatively connected to the ultrasonic wave generation probe, the processing unit being configured to:
      determine which of the first plurality of positioning marks has been detected based on the reflection time, and
      display an instruction to displace the ultrasonic wave generation probe in a specified direction based on which of the first plurality of positioning marks has been detected.

9. The assembly according to claim 8, wherein each positioning mark of the first plurality of positioning marks comprises:
   a substrate having a first acoustic impedance, and
   an element having a second acoustic impedance, wherein the element is at a depth within the substrate, wherein the depth of the element is different for each positioning mark of the first plurality of positioning marks.

10. The assembly according to claim 8, wherein each positioning mark of the first plurality of positioning marks comprises a blind hole having a different depth from any other positioning mark of the first plurality of positioning marks.

11. A method for imaging or treating a brain tissue of a patient, the method comprising:
   detecting, by operating an ultrasound device in a first mode of operation, a first positioning mark of a plurality of positioning marks integrated in an acoustic window implanted at an opening in the cranium of the patient, wherein the acoustic window is covered with the skin of the patient's skull, wherein the acoustic window comprises a plate transparent to ultrasonic waves, wherein the plurality of positioning marks are detectable by ultrasonography, and wherein each of the positioning marks comprises a blind hole having a different depth from any other positioning mark of the plurality of positioning marks;
   determining, based on a reflection time corresponding to the positioning mark, which positioning mark of the plurality of positioning marks has been detected;
   displaying, based on the determining, an instruction to displace the ultrasound device in a specified direction;
   after detecting, by the ultrasound device, all positioning marks of the plurality of positioning marks, sending an instruction to maintain the ultrasound device in a stationary position; and
   applying, by the ultrasound device operating in a second mode of operation, ultrasonic waves to the patient, wherein the second mode of operation corresponds to an imaging mode or a treating mode.

12. The method of claim 11, wherein the first mode is a location mode.

13. The method of claim 12, wherein the location mode is an A-mode ultrasonography.

14. The method of claim 11, wherein after detecting, by the ultrasound device, all positioning marks of the plurality of positioning marks, the method further comprises:
   removing the ultrasound device;
   applying a transmission gel onto the patient above the acoustic window based on the detected plurality of positioning marks; and
   re-positioning the ultrasound device in line with the acoustic window.

* * * * *

UNITED STATES PATENT AND TRADEMARK OFFICE
CERTIFICATE OF CORRECTION

| | | |
|---|---|---|
| PATENT NO. | : 12,029,652 B2 | Page 1 of 1 |
| APPLICATION NO. | : 16/623974 | |
| DATED | : July 9, 2024 | |
| INVENTOR(S) | : Alexandre Carpentier et al. | |

It is certified that error appears in the above-identified patent and that said Letters Patent is hereby corrected as shown below:

On the Title Page

In the Item (73) Assignee section, the name of the second Assignee "SORBONNE UNIVERSITY" should read --SORBONNE UNIVERSITE--

Signed and Sealed this
Thirteenth Day of August, 2024

Katherine Kelly Vidal
*Director of the United States Patent and Trademark Office*